(12) United States Patent
Strickland et al.

(10) Patent No.: US 9,386,943 B2
(45) Date of Patent: Jul. 12, 2016

(54) HANDHELD EXTREMITY FLEXIBILITY EVALUATION AND TREATMENT DEVICE

(76) Inventors: Roger Nicholas Strickland, Wilmington, DE (US); Joseph Michael Dawson, III, Wilmington, DE (US)

( * ) Notice: Subject to any disclaimer, the term of this patent is extended or adjusted under 35 U.S.C. 154(b) by 627 days.

(21) Appl. No.: 13/361,040

(22) Filed: Jan. 30, 2012

(65) Prior Publication Data
US 2013/0197398 A1 Aug. 1, 2013

(51) Int. Cl.
| | | |
|---|---|---|
| A61B 5/103 | (2006.01) | |
| A61B 5/11 | (2006.01) | |
| A61B 5/22 | (2006.01) | |

(52) U.S. Cl.
CPC ................. *A61B 5/11* (2013.01); *A61B 5/1121* (2013.01); *A61B 5/224* (2013.01)

(58) Field of Classification Search
CPC .... A61B 5/4528; A61B 5/1071; A61B 5/103; A63B 21/0552; A63B 21/0442; A63B 21/0557
USPC .......... 600/587, 595; 482/5, 8, 121, 122, 125, 482/126
See application file for complete search history.

(56) References Cited

U.S. PATENT DOCUMENTS

| | | | | |
|---|---|---|---|---|
| 5,538,486 A * | 7/1996 | France et al. | | 482/8 |
| 6,210,348 B1 * | 4/2001 | Reed | | A61H 1/0292 482/72 |
| 6,634,995 B1 * | 10/2003 | Reed | | A63B 21/153 482/132 |
| 7,361,126 B2 * | 4/2008 | Bruce | | 482/121 |
| 7,563,207 B1 | 7/2009 | Burek | | |
| 7,652,953 B1 | 1/2010 | Fluegge | | |
| 8,075,462 B1 * | 12/2011 | Hinds et al. | | 482/125 |
| 8,475,345 B2 * | 7/2013 | Wang | | 482/122 |
| 2003/0093884 A1 * | 5/2003 | Doty | | 24/302 |
| 2003/0106187 A1 * | 6/2003 | Jackson et al. | | 24/298 |
| 2004/0157710 A1 * | 8/2004 | Basting | | 482/126 |
| 2004/0190383 A1 * | 9/2004 | Marcucelli et al. | | 368/278 |
| 2004/0204302 A1 * | 10/2004 | Flynn | | 482/124 |
| 2006/0201450 A1 * | 9/2006 | Jordan | | A01K 27/004 119/796 |
| 2010/0016132 A1 * | 1/2010 | Flynn | | 482/122 |
| 2010/0261583 A1 * | 10/2010 | Ferguson et al. | | 482/79 |
| 2011/0204306 A1 * | 8/2011 | Kingery | | 254/391 |
| 2011/0251021 A1 * | 10/2011 | Zavadsky et al. | | 482/5 |

\* cited by examiner

*Primary Examiner* — Sean Dougherty
*Assistant Examiner* — Daniel Cerioni

(57) ABSTRACT

A handheld tissue stretching device combined with an extremity flexibility number, stretchscore, enables users to independently evaluate and treat the flexibility of their extremity tissue minimizing physical therapist intervention to evaluate and treat tissue. The distance between handheld stretching devices and the extremity supports changes with a high degree of variability during home treatments; whereas, medical professionals monitor stretch intensity visually and manually. Patients performing home-based stretches impart variable intensity that leads to inconsistent tissue treatment resulting in increased tissue stiffness. The present inventors have discovered when the slack is automatically retracted, the distance between the users hands and the extremity support is continuously proportional to the flexibility of the extremity. This "distance matching" between the handheld stretching device and the extremity support provides a reliable, repeatable, and independent evaluation of extremity flexibility by directly relating this change in distance to the user's flexibility.

2 Claims, 5 Drawing Sheets

— Prior Art —

— Prior Art —

HANDHELD EXTREMITY FLEXIBILITY EVALUATION AND TREATMENT DEVICE

BACKGROUND OF THE INVENTION

The present invention relates to tissue evaluation and treatment. Physical therapists are trained to evaluate and treat a wide variety of musculoskeletal conditions including muscle strain, joint sprain as well as insidious onset of spine and extremity pain. Tissue evaluation involves techniques including assessment of joint range of motion (ROM), extremity flexibility, and strength testing. Patients rely on a these specialists to provide an extremity flexibility evaluation with a goniometer reported in degrees. Measurement of extremity flexibility is referred to as "evaluation". Extremity treatment provided by specialists often includes includes passive stretching, massage and strengthening exercises. Home-based treatments including passive stretching are prescribed by medical professionals to reduce patients' long term pain. Passive stretching by medical professionals is a common treatment which increases extremity flexibility to relieve lower back pain, patellofemoral syndrome (knee pain), nerve entrapment (sciatica), plantar fasciitis, achilles tendon tightness, and various tendonopathies. Treatment regimens include a stretch intensity, duration, and frequency of each exercise. Patients perform prescribed treatments at home by using a towel, belt, or a strap such as the "stretch-out-strap" by OPTP products. Stretching to increase extremity tissue length and flexibility is referred to as "treatment".

At home, many patients do not have a way to evaluate their flexibility and often fail to comply with the prescribed treatment regimen. Over time tissue stiffness increases and reduces muscle-sinew tissue compliance, noted as the degree to which the muscle-sinew tissue complies to treatment. This decrease in muscle-sinew tissue compliance often leaves patients wondering what their flexibility is and what treatment regimen to follow to achieve acceptable flexibility. The solution to evaluating their flexibility and determining the new treatment regimen is to return to the clinic, have a physical therapist evaluate their tissue flexibility using a goniometer and prescribe a flexibility treatment regimen. This can be a costly, time consuming, and often painful approach to maintaining optimal flexibility.

BRIEF SUMMARY OF THE INVENTION

The known handheld tissue stretching devices do not allow the user to objectively evaluate tissue flexibility nor provide a consistent treatment treatment intensity because of the constant repositioning needed to change treatment intensity. Evaluating and treating tissue with existing handheld devices leaves the user wondering whether or not he has stretched properly. Pain is often the feedback individuals use to determine their extremity flexibility regimen. Over time, changes in compliance of the muscle-sinew tissue may alter the needed treatment regimen making a proper evaluation and treatment regimen even more difficult for the user. Combining a reliable extremity flexibility evaluation with a handheld tissue stretching device eliminates pain as the primary means for feedback and provides other benefits such as minimizing trips to the physical therapy clinic, decreasing the risk of activity-based injuries, and optimizing tissue treatment intensity, duration and frequency to achieve desired extremity flexibility. Individuals now have the option of reliably and independently evaluating their extremity flexibility and properly treating their muscle-sinew combinations before engaging in activities such as walking, running, sports or work activities.

In accordance with the invention, a handheld tissue stretching device combined with an extremity flexibility number enables users to reliably and independently evaluate and treat the flexibility of their extremity tissue; thereby, minimizing physical therapist intervention to evaluate and prescribe a treatment regimen. Similar to a scale used to measure an individual's weight, the extremity flexibility number provides an immediate evaluation of a user's extremity flexibility. Until now, patients have depended upon someone else to determine their flexibility values and issue a flexibility treatment regimen to be done in accordance with this evaluation. The present inventors, however, have recognized that combining a handheld tissue stretching device with an extremity flexibility evaluation, in the form of an extremity flexibility number, will provide users with a simple indicator of extremity flexibility. Such an extremity flexibility number is referred to herein as a "stretchscore".

Treatment intensity is carefully monitored by medical professionals by verbal, visual and manual inspections to provide a consistent treatment. Outside of the clinic however, handheld passive stretching devices cannot provide users with a reliable and consistent treatment. The known treatment devices have an extremity support, to engage the extremity to be treated, and link between the extremity and the users hands. The user changes the intensity of the stretch by pulling the extremity support is engaged with the extremity. Pulling the extremity increases muscle-sinew tissue length of the tissue being treated. The user has to reposition his hands on the device or move his hands relative to the extremity support to change stretch intensity. The distance between the users hands and the extremity support remains constant and the user has to reposition his hands, this repositioning is inconsistent and imparts a high degree of intensity variability during treatment. When patients are performing home-based stretches, variable intensity can lead to inconsistent tissue treatment resulting in increased tissue stiffness. The present inventors have discovered a way to increase stretch intensity consistency during self treatment of muscle-sinew tissue. When a user increases the stretch intensity, the slack in the pliable, inelastic link, caused by pulling the extremity, is automatically retracted, and the distance between the users hands and the extremity support is continuously proportional to the tissue length of the extremity. This "distance matching" between the handheld stretching device and the extremity support provides a reliable, repeatable, and independent treatment method and evaluation of extremity flexibility. This method of treatment, when used in combination with a stretchscore, provides an evaluation of tissue flexibility to the user ensuring a consistent and purposeful treatment regimen.

In another embodiment, pulling force may be used to indicate the stretchscore. Treatment intensity is directly matched to the amount of force the user imparts on the extremity when pulling on the extremity support. The amount of force needed to stretch an extremity is referred to as "passive resistance to stretch" or tensile force of the muscle-sinew tissue. Tests showed this pulling force ranged from about 4 pounds force to about 20 pounds force. Decreasing passive resistance to stretch at a given range of motion increases tissue flexibility; this is known as the viscoelastic effect. The present inventors have discovered a consumer friendly way to translate the "passive resistance to stretch" into an evaluation of tissue flexibility in the form of a stretchscore.

In another embodiment, the pulling force was impacted by an unexpected factor. The inventors have discovered that, in addition to passive resistance to stretch of the muscle-sinew combination, the weight of the extremity increases the pulling force required to provide acceptable treatment intensity. The extremity weight increased the pulling force up ranging from about 5-50 pounds force, depending on how parallel the extremity was with the support surface, and led the inventors to seek methods to reduce the pulling force caused by extremity weight. Increased pulling force requires users to have significant grip strength to impart a reliable and repeatable passive stretch and maintain optimum flexibility. The pulling force required to overcome the weight of the extremity was substantially increased as the extremity was more parallel to the support surface. As the extremity was brought into a perpendicular orientation to the support surface the pulling force needed to overcome the weight force reduced to zero.

The stretchscore may be determined for lower extremities encompassing all tissue emanating from the lower back and terminating at the phalanges. The stretchscore may also be determined for upper extremities encompassing all tissue emanating from the scapula and terminating at the phalanges. In one context, a stretchscore extremity flexibility number is displayed to the user within a range of possible scores up to and including a maximum.

DETAILED DESCRIPTION OF THE INVENTION

Figure 1:
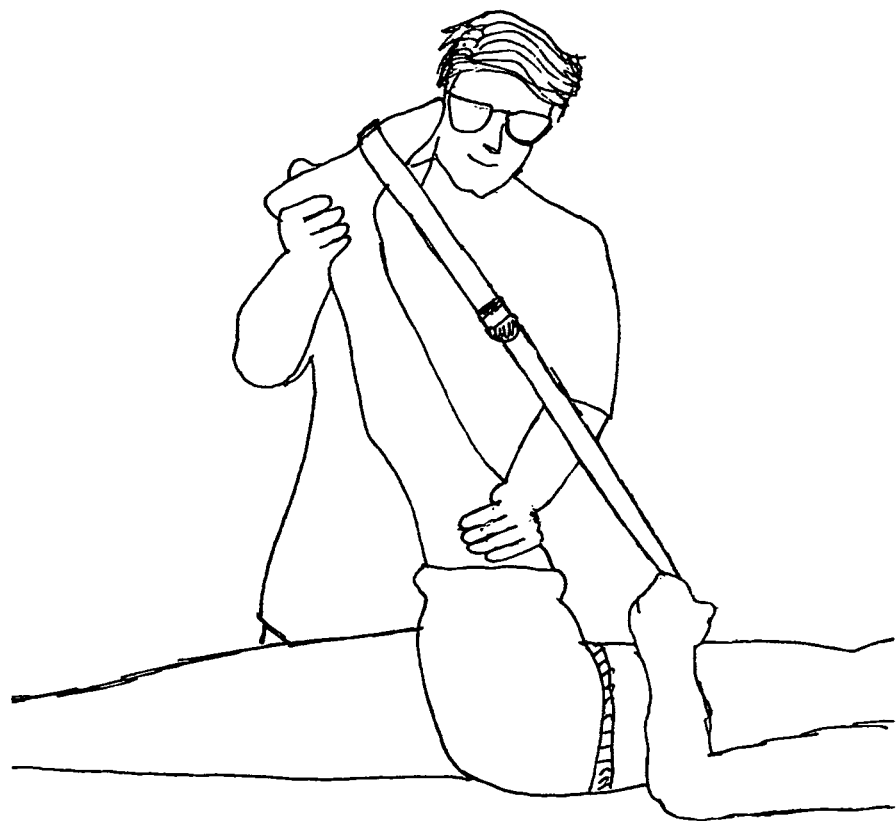
FIG. 1 depicts prior art showing a medical professional assisting a patient to treat muscle tissue using an assisted straight leg stretch. The patient is using an inelastic adjustable strap placed on the foot and the physical therapist provides overpressure and feedback to maintain knee extension while assisting with hip flexion.
Figure 2:
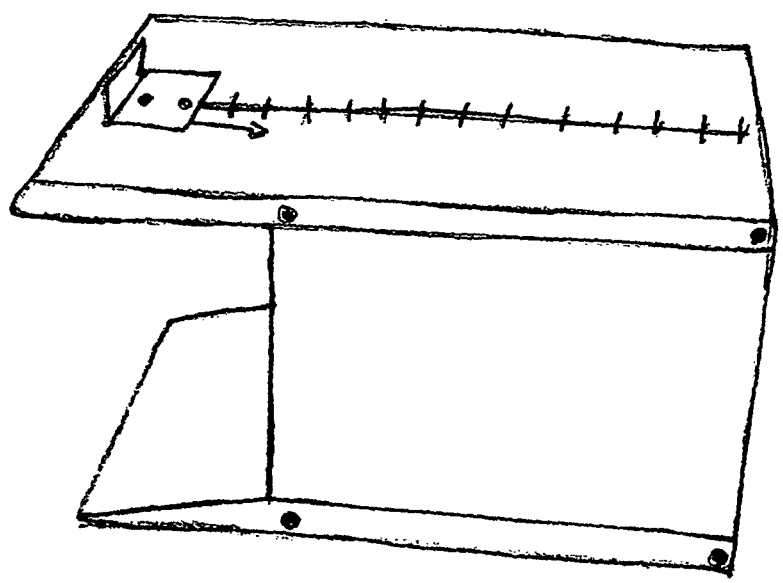
FIG. 2 depicts prior art in product called Acuflex I modified sit and reach device by Novel Products for evaluating lumber and hamstring flexibility. The Acuflex I does not provide a means for tissue treatment.

FIG. 1 shows the prior art practice of a medical professional treating treating extremity tissue. The user is performing a passive stretch on the posterior lower extremity by holding a strap that is releasably engaged with the extremity by wrapping the strap around the metatarsal pad of the foot. FIG. 2 shows a device that a user may place his feet on and push a slidable indicator along a track to provide the user with a indication of the user's lumbar and hamstring flexibility. The device weighs approximately 15 pounds and is bulky. The device does not provide a means for treatment. An apparatus described in the Burek patent shows a large stationary device for stretching and evaluating tissue using several measures.

The known portable tissue stretching devices do not properly allow the user to control the treatment intensity because of the need to reposition when increasing stretch intensity, and leave the user wondering whether or not he has stretched properly; known portable flexibility evaluation devices are bulky and most do not provide a means for passively stretching muscle-sinew tissue. Changes in compliance of the muscle-sinew tissue over time can demand different treatment regimens and confuse individuals; pain is often the evaluation method individuals use to determine their extremity flexibility treatment. A self flexibility evaluation is complex because of tightness of specific muscle-sinew combinations, co-morbidities, and the time since last stretch. An apparatus described in the Fluegge patent incorporates a timer that indicates elapsed time for a given stretch. However, elapsed time does not provide an evaluation of the extremity flexibility. Combining an extremity flexibility evaluation, in the form of an extremity flexibility number 2, with a handheld tissue stretching device provides numerous benefits such as minimizing trips to the physical therapy clinic, eliminating pain as feedback for flexibility evaluation, decreasing the risk of activity-based injuries, increasing muscle-sinew tissue compliance, and optimizing tissue treatment intensity, duration and frequency to achieve desired extremity flexibility. Individuals now have the option to independently and reliably evaluate and improve their flexibility before engaging in activities such as walking, running, sports or work activities.

Figure 3:
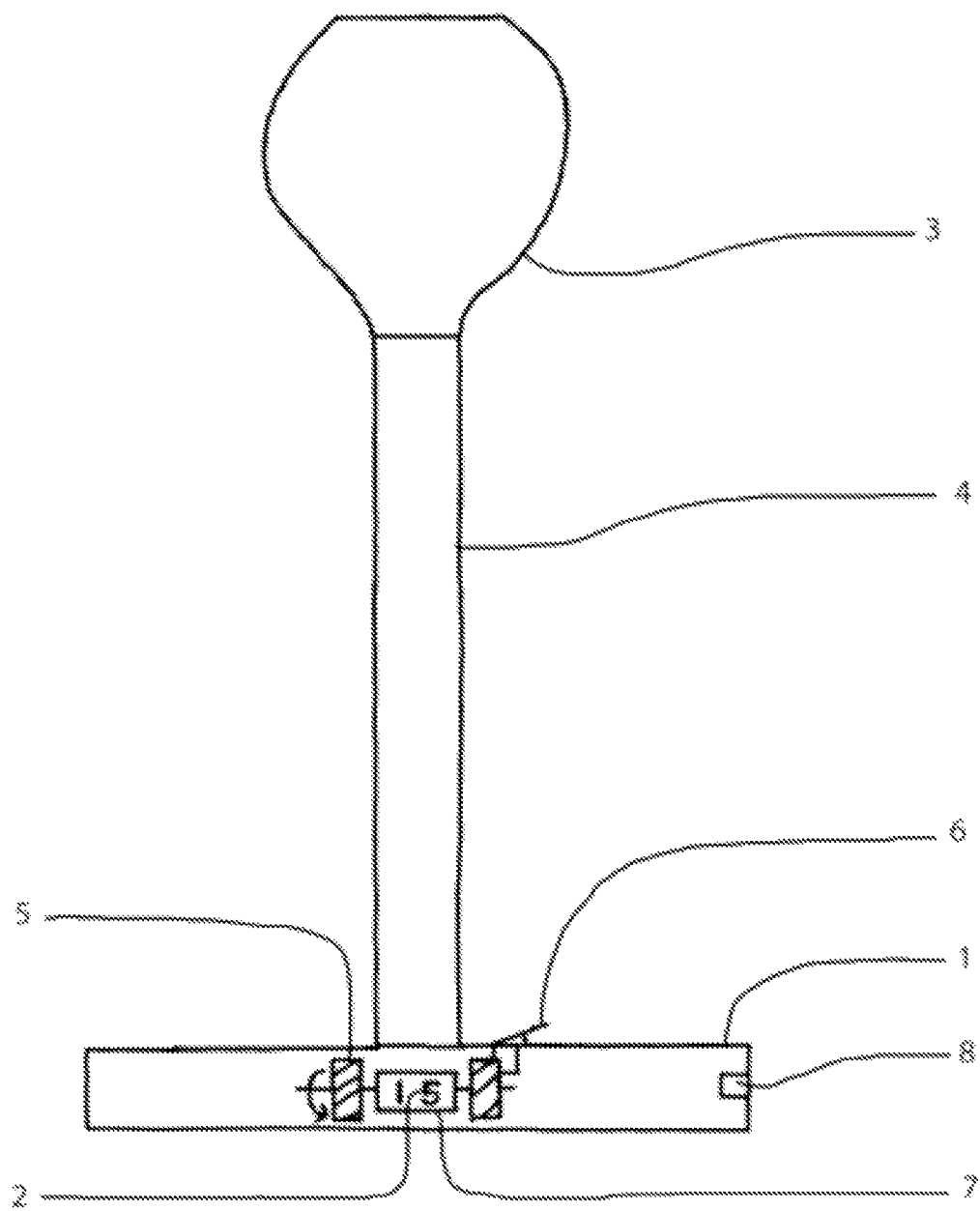
FIG. 3 depicts one embodiment of the present invention, a handheld tissue stretching device that displays an extremity flexibility number to the user when the extremity support is engaged with the users extremity.

In accordance with the invention, FIG. 3 depicts one embodiment of the invention, a handheld tissue stretching device 1 that provides an extremity flexibility number 2 that an individual may use for both evaluating and treating extremity flexibility without involving another person. This device has an extremity support 3 that may be releasably engaged to the user's extremity for evaluation and treatment. The extremity support 3 is connected to the handheld tissue stretching device 1 via a pliable, inelastic link 4. A retractor 5 pulls the pliable inelastic link 4 and extremity support 3 toward the handheld tissue stretching device 1. A release mechanism 6 is used to disengage the retractor and allow the user to extend the extremity support 3 away from handheld tissue stretching device 1. This device 1 enables users to evaluate and treat the flexibility of their extremity tissue as needed, minimizing physical therapist intervention to prescribe a treatment regimen. Similar to a scale used to measure an individual's weight, the extremity flexibility number 2 provides an immediate evaluation of a user's extremity flexibility. Until now, patients have depended upon someone else to determine their flexibility values and issue a flexibility treatment regimen to be done in accordance with this evaluation. The present inventors, however, have recognized that combining a handheld tissue stretching device 1 with an extremity flexibility evaluation, in the form of a display 7 capable of showing an extremity flexibility number 2, will provide users with a simple indicator of extremity flexibility. A communication means 8 may be provided to share the stretchscore with an electronic device.

Figure 4:
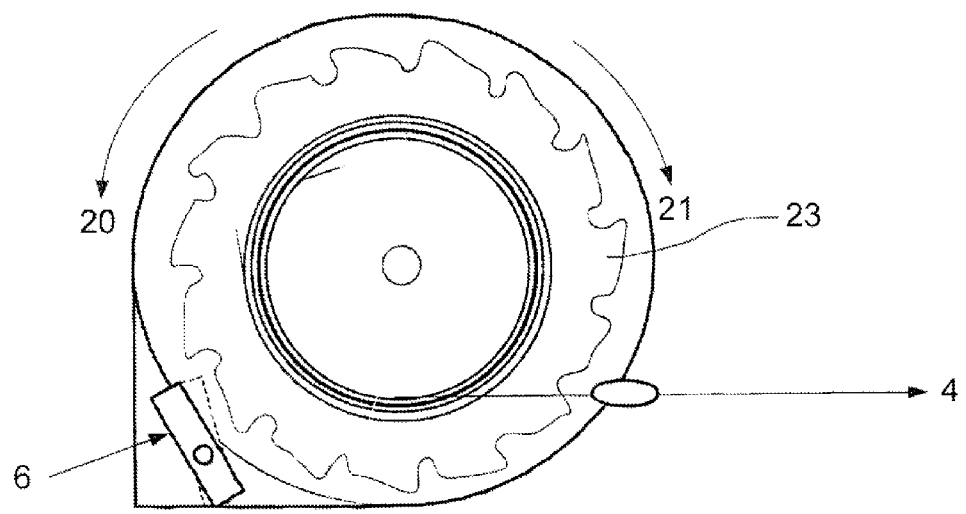
FIG. 4 depicts one embodiment of the present invention, a retractor is used to remove the slack 21 in the pliable, inelastic link 4 when the extremity support 3 is pulled toward the handheld tissue stretching device 1. The retractor prevents the extremity support 3 from extending 20 away from the handheld tissue stretching device 1 when providing treatment.

FIG. 4 shows one embodiment of a retractor. The pliable, inelastic link 4 may be pulled toward the handheld tissue stretching device 21. A release mechanism 6 when engaged with the retractor gear 23 prevents the pliable, inelastic link 4 from extending away from the handheld tissue stretching device 20. The release mechanism 6, when disengaged with the retractor gear 23 allows the pliable inelastic link 4 to be extended 20 away from the handheld tissue stretching device 1.

Figure 5:
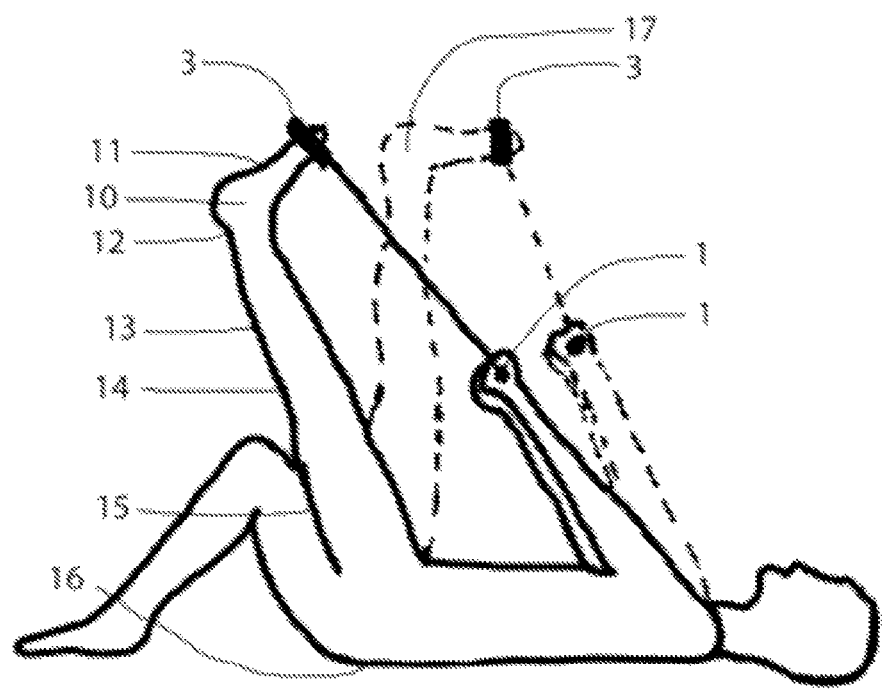
FIG. 5 depicts one embodiment of the present invention. The user is treating tissue by pulling the lower extremity from a first position 10 to a second position 17 to impart a passive stretch on the posterior lower extremity tissue. The handheld stretching device 1 displays an extremity flexibility number 2 to the user in both positions.

FIG. 5 shows a particular method employing one embodiment of the invention, a user stretching the posterior lower extremity. The user holds the handheld tissue stretching device 1 in his hands and engages the extremity support 3 on the metatarsal foot pad in a relaxed position 10, the user then increases the intensity of the stretch actively raising his extremity and simultaneously pulling on the handheld tissue stretching device 1 the retractor 5 pulls the extremity support 3 toward the handheld stretching device 1 and removes the occurring slack in the pliable, inelastic link 4 as the tissue being treated is lengthened. The plantar fascia tissue 11, the achilles tendon 12, the calf musculature 13, the popliteal fossa 14, the hamstring muscle group 15, and the lower back muscles and sinew 16 begin to lengthen as the user pulls the extremity to the second position 17. The user then reads the extremity flexibility number 2 in the passive stretching position 17. A shorter distance between the extremity support 3 and the handheld tissue stretching device 1 corresponds directly to lengthening the tissue of the posterior lower extremity: plantar fascia tissue 11, the achilles tendon 12, the calf musculature 13, the popliteal fossa 14, the hamstring muscle group 15, and the lower back 16. An extremity flexibility number 2 is displayed to the user any time the extremity is engaged with the extremity support 3; the user may adjust treatment based on the extremity flexibility number 2. The user may disengage the release mechanism 6 from the retractor gear 23 to extend 20 the extremity support 3 away from the handheld tissue stretching device 1 and allow the user to lower the extremity to the support surface.

The stretchscore extremity flexibility number 2 can be obtained in numerous ways. One embodiment for determining the stretchscore measures the distance between the handheld tissue stretching device 1 and user's extremity when the extremity is engaged with an extremity support 3. A pliable, inelastic link 4 is used to connect the extremity support 3 to the handheld tissue stretching device 1. The handheld tissue stretching device 1 has a retractor 5 that retracts 21 the pliable, inelastic link 4 as the extremity support 3 moves toward the handheld tissue stretching device 1. Minimizing this distance enables users to eliminate continuous and variable hand repositioning on the handheld tissue stretching device 1 in order to change the intensity of the flexibility treatment. This "distance matching" between the handheld stretching device 1 and the extremity support 3 provides a reliable, repeatable, and independent evaluation of extremity tissue flexibility in the form of an extremity flexibility number 2. The concept of using distance matching in a handheld tissue treatment device is an invention independent of the present invention and is the subject of a separate application being filed by the present inventor on the same day as this application.

In another embodiment, pulling force may be used to indicate the extremity flexibility number 2. Treatment intensity is one of the three elements of a treatment regimen and is related to the amount of pulling force the user imparts on the extremity. The amount of force needed to stretch an extremity tissue can be measured and is referred to as "passive resistance to stretch" or tensile force of the muscle-sinew combination. Decreasing passive resistance to stretch is directly matched to increasing tissue flexibility; this is known as the viscoelastic effect. The present inventors have discovered that the passive resistance to stretch of the muscle-sinew tissue combined with the weight of the extremity equals the pulling force between the extremity support 3 and the handheld tissue flexibility device 1. During most treatment regimens, the weight of the extremity adds a substantial opposing force that must be overcome by the pulling force; the added pulling force make it difficult for the user to maintain adequate pulling force and increases variability of the stretch intensity. The combination of the weight of the extremity and the passive resistance to stretch has been measured to be an excellent predictor of the extremity flexibility number 2.

In another embodiment of the invention, the pulling force and the distance between the handheld tissue stretching device 1 and the extremity support 3 were combined to compute an extremity flexibility number 2. Transforming these two measurements into a single extremity flexibility number 2 provides the user with a individualized evaluation of extremity flexibility. These measurements are taken any time the user holds the handheld tissue stretching device 1 and engages the extremity with the extremity support 3.

In a particular embodiment of the invention, the user improves the extremity flexibility number 2 when performing a passive stretch 17 on the lower posterior tissue by bending the contralateral lower extremity. The present inventors have shown immediate improvements in the ease of obtaining a stretchscore extremity flexibility number 2 explained by bending the contralateral extremity. This bending of the contralateral extremity allow the extremity being stretched to become more perpendicular to the support surface. When the ipsilateral extremity becomes more perpendicular to the support surface, the pulling force required between the handheld tissue stretching device 1 and the extremity support 3 is reduced because the downward component of the weight does not have to be overcome by the pulling force. Reducing the pulling force using this method enables users to maintain stretch intensity and requires less upper body and hand strength. A flexibility method requiring less grip strength is desirable for persons with weak grip or weak upper body strength.

The extremity flexibility number 2 may be determined for lower extremities encompassing all tissue emanating from the lower back and terminating at the phalanges. The extremity flexibility number 2 may also be determined for upper extremities encompassing all tissue emanating from the scapula and terminating at the phalanges. In one context, an extremity flexibility number 2 is displayed to the user within a range of possible scores up to and including a maximum extremity flexibility number 2.

In a particular embodiment, the extremity flexibility number 2 may be communicated to an electronic network or device using a communication means 8.

Other measurements may include one or a combination of angle, or moment between handheld extremity flexibility treatment device 1 and extremity support 3.

We claim:

1. A handheld tissue evaluation and stretching apparatus configured to simultaneously stretch a user's tissue or muscles and objectively evaluate the user's lower extremity tissue or muscle flexibility, the apparatus comprising:
   a handheld tissue stretching device located at a first end of the handheld tissue evaluation and stretching apparatus, the handheld tissues stretching device being configured to be grasped by a hand of the user, and the handheld tissue stretching device including:
   a display, the display configured to display a flexibility number, the display disposed on a most proximal face of the handheld tissue evaluation and stretching apparatus; wherein, the display is configured for the user to read the display when using the apparatus while performing a posterior lower extremity stretch;
   a retractor;

a retractor gear; and
a release mechanism;
an extremity support located at a second end of the handheld tissue evaluation and stretching apparatus, the extremity support being configured to be releasably engaged with a foot of the user; and
a pliable link extending between the first end and the second end, the pliable link being in direct contact with the retractor and the pliable link being in direct contact with the extremity support;
wherein the flexibility number is a value representing a direct measurement of a distance between the user's hand holding the first end and the user's foot releasably engaged with the second end, the value of the flexibility number being greater when the, distance between the first and second end is smaller and the value of the flexibility number is lesser when the distance between the first end and the second end is larger such that the flexibility number value indicates a tissue or muscle flexibility of the user.

2. The apparatus of claim 1, wherein said handheld tissue stretching device is configured to transmit said extremity flexibility number to an electronic network or device.

* * * * *